United States Patent
Hsieh et al.

(10) Patent No.: US 8,354,729 B2
(45) Date of Patent: Jan. 15, 2013

(54) GAS SENSOR AND MANUFACTURING METHOD THEREOF

(75) Inventors: Yu Sheng Hsieh, Zhubei (TW); Jing Yuan Lin, Tucheng (TW); Shang Chian Su, Wugu Township, Taipei County (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 93 days.

(21) Appl. No.: 12/979,002

(22) Filed: Dec. 27, 2010

(65) Prior Publication Data
US 2012/0161253 A1    Jun. 28, 2012

(51) Int. Cl.
*H01L 41/08* (2006.01)
(52) U.S. Cl. ........ 257/414; 257/415; 257/417; 257/419; 257/E21.211; 438/52; 438/53; 438/48; 381/75; 381/355; 381/360; 381/369
(58) Field of Classification Search .................. None
See application file for complete search history.

(56) References Cited

U.S. PATENT DOCUMENTS
| | | | |
|---|---|---|---|
| 6,161,421 A | 12/2000 | Fang et al. | |
| 7,157,054 B2 | 1/2007 | Toyoda et al. | |
| 7,253,488 B2 * | 8/2007 | Zhan et al. | 257/414 |
| 7,296,458 B2 | 11/2007 | Dimeo, Jr. et al. | |
| 7,495,300 B2 | 2/2009 | Gardner et al. | |

OTHER PUBLICATIONS

Gwly-Sang Chung, "The Fabrication of Micro-Heaters with Low-Power Consumption Using SOI and Trench Structures," Metals and Materials International, vol. 8, No. 4 (2002), pp. 347-351.
T Iwaki, J A Covington, F Udrea, S Z Ali, P K Guha and J W Gardner, "Design and simulation of resistive SOI CMOS micro-heaters for high temperature gas sensors," Journal of Physics, Conference Series 15, Sensors & their Applications XIII , 2005, 27-32.
J. Spannhake et al., "SnO2:Sb—A new material for high-temperatue MEMS heater applicatons: Performance and limitations," Sensors and Actuators B 124, 2007, 421-428.

* cited by examiner

*Primary Examiner* — Fei Fei Yeung Lopez
(74) *Attorney, Agent, or Firm* — Egbert Law Offices, PLLC

(57) ABSTRACT

A gas sensor manufacturing method including the following steps: providing a SOI substrate, including an oxide layer, a device layer, and a carrier, wherein the oxide layer is disposed between the device layer and the carrier; etching the device layer to form an integrated circuit region, an outer region, a trench and a conducting line, the conducting line including a connecting arm connecting to the integrated circuit region, the trench is formed around the conducting line and excavated to the oxide layer for reducing power consumption of the heater circuit, the connecting arm reaches over a gap between the integrated circuit region and the outer region and electrically connects to the integrated circuit region; coating or imprinting a sensing material on the circuit region; and etching the carrier and the oxide layer to form a cavity to form a film structure suspended in the cavity by the cantilevered connecting arm.

9 Claims, 12 Drawing Sheets

GAS SENSOR AND MANUFACTURING METHOD THEREOF

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The disclosure relates to a gas sensor. More particularly, the disclosure relates to a micro-semiconductor gas sensor.

2. Description of Related Art Including Information Disclosed Under 37 CFR 1.97 and 37 CFR 1.98.

A gas sensor is one kind of sensor device for detecting gas concentration. Generally, gas sensors are utilized to monitor for leakage of toxic gas, environmentally harmful gas, combustible gas, and explosive gas for early warning in process control. Gas sensors are also used for home applications. For instance, a gas sensor can be used to detect fuel gas and carbon monoxide leaks to protect people in the house. In addition, an alcohol sensor can be used to detect breath-alcohol concentration in persons suspected of driving under the influence of alcohol. In addition, gas sensors can be utilized in vehicles such as automobiles to monitor engine combustion efficiency and exhaust gas emissions. Currently, rapidly increasing numbers of home, automobile, and wireless network applications require increasing numbers of gas sensors. According to a global survey conducted in 2001, the global market of gas sensors was about 2.3 billion dollars and the report estimated that with an annual mean growth rate of about 5.9%, the global market would reach 3.5 billion dollars.

Gas sensors are categorized by the gas detected or by the type of sensor. There are many different types of gas sensor including electrochemical, solid-state electrolyte, optical, metal oxide semiconductor, and others. Early gas sensor used a liquid electrochemical mechanism. The early gas sensor has been largely replaced by solid-state electrolyte gas sensors, which are more easily miniaturized. However, optical gas sensors require complicated optical systems. Current solid-state electrolyte gas sensor designs include catalyst with flame, metal oxide semiconductor, solid-state ion-conductor, and field-effect transistors.

The first commercial semiconductor gas sensor was produced by Figaro Eng, Inc. in 1967. This Taguchi-type gas sensor was utilized for detecting alcohol, fuel, and other gas. The Taguchi-type gas sensor is composed of a metal heating coil (such as a platinum coil), a metal oxide semiconductor sensing material coating on the metal heating coil, and sensing electrodes disposed at two terminals of the sensing material. The metal heating coil coated with the sensing material and the sensing electrodes are cantilevered in a TO can to form a tubular sensing structure.

Researchers have developed another semiconductor gas sensor manufactured using thick film technique. The thick-film gas sensor is imprinted by stencils. Because the stencil can imprint the heater circuit, gas sensing circuit, and sensing material on the ceramic plate, it is possible to manufacture in batches.

Since most semiconductor gas sensors are required to operate under predetermined high temperature to achieve consistency, sensitivity, and reactivity, the heater circuit provides a high temperature micro-environment for operation of the gas sensor. Although both the Taguchi-type gas sensor and the stencil-imprinting gas sensor use the metal conducting line to cantilever the sensing material in the package to avoid unnecessary heat emission, power consumption of both of these gas sensors is still greater than 1 watt. For the purposes of miniaturizing components and reducing power consumption, in the 1980's, researchers developed the Micro Electro Mechanical Systems (MEMS) technique to fabricate micro gas sensors. The micro gas sensor is fabricated on a wafer substrate by a process similar to the semiconductor process, allowing the micro gas sensor to be manufactured in batches and easily miniaturized on a silicon chip with signal amplifier.

Since the micro gas sensor is fabricated on the silicon wafer, which has a thermal conductivity greater than that of ceramic material, the micro gas sensor requires more consideration of the thermal conductive paths to minimize heat emission on the silicon substrate. Thus, most types of MEMS gas sensors are produced by etching a silicon substrate to form a very thin film as a gas sensing region and to reduce power consumption. There are two types of thin film structure of the gas sensors including a close-membrane type and a suspended-film type. The close-membrane type gas sensor has a gas sensing region in an enclosed film. The suspended-film type has its gas sensing region on a thin film suspended by several cantilevered beams. In the structural view, the heat emission paths are limited to the cantilevered beam in the suspended-film type gas sensor; therefore, the suspended-film type gas sensor has much lower power consumption, but its thin film structure is vulnerable.

The films of common close-membrane type gas sensors are formed through deposition of dielectric such as silicon oxide, silicon nitride, and so on. The heater circuit and temperature sensing circuit are formed inside of the film of the close-membrane package. The gas sensing electrodes and sensing material are disposed on the film. Since the film includes many layers with different thermal expansion coefficients, the inner stress of the film due to unequal thermal expansion coefficients will distort or even crack the sensing film. In addition, since the temperature of the gas sensor fluctuates between high operating temperature and room temperature, the sensing film of the close-membrane type gas sensor has several layers that are vulnerable due to different thermal expansion coefficients among these layers. For suspended-film type gas sensors, there is a challenge in integrating the sensing material and the sensing film. Under high operating temperatures, the metal heater circuit can be destroyed due to metal deterioration.

U.S. Pat. No. 6,161,421 discloses a gas sensor for detecting alcohol including a cantilever bridge composed of silicon carbide, SiC as a sensing film and a heater circuit. The SiC film includes sensing electrodes and the sensing material for detecting alcohol in the air.

U.S. Pat. Nos. 7,495,300 and 7,157,054 disclose MEMS gas sensors, both of which are formed on the silicon on insulator, Silicon-on-Insulator (SOI) wafer substrate. Both of these gas sensors can be fabricated using standard CMOS or BiCMOS processes incorporating post-CMOS MEMS process. One characteristic of these gas sensors is that the amplifier circuit and the operating circuit are fabricated on the same chip. The difference between the above patents is that U.S. Pat. No. 7,495,300 utilizes tungsten in the CMOS process to form the heater circuit in the micro-gas sensor, whereas U.S. Pat. No. 7,495,300 utilizes polysilicon in the CMOS process to form the heater circuit in the gas sensor. Such film is vulnerable due to the inner stress from different thermal expansion coefficients among the layers in the film.

J W Gardner et al, Journal of Physics: Conference Series, 15, pp. 27-32, 2005, proposed an integrated micro-gas sensor in the SOI wafer substrate. The micro-gas sensor can integrate with a MOSFET circuit in the same chip. The heater circuit of the gas sensor is composed of a monosilicon layer in SOI wafer substrate, wherein the power consumption of the monosilicon heater circuit is less than that of polysilicon heater circuit or metal heater circuit in a high temperature operating situation. However, the sensing film of the gas sensor is also vulnerable in high temperature operating situations due to its layers including different materials with different thermal expansion coefficients.

Gwiy-Sang Chung, Metals and Materials International, Vol. 8, No. 4, pp. 347-351, 2002, proposed a micro-gas sensor in the SOI wafer substrate. One characteristic of the gas sensor manufacturing process is the etching of the sensing film to form a groove and then to insert silicon oxide into the groove. The paper presented that the maximum heating temperature of the gas sensor without any groove is 280 degrees Celsius; however, the maximum heating temperature of the gas sensor with ten rounds of the above-mentioned grooves is 580 degrees Celsius.

BRIEF SUMMARY OF THE INVENTION

A feature of the disclosure is to provide a gas sensor having a trench formed around the conducting line and excavated to the oxide layer to reduce power consumption during operation. Another feature of the disclosure is to provide a gas sensor having a device layer of a predetermined thickness. Thus, the gas sensing film of the disclosure is relatively stable, and suited for integrating gas sensor components with the sensing material.

Another feature of the disclosure is to provide a gas sensor having a silicide layer formed in the conducting line connected to the heater circuit. Since the electrical resistance of the silicide layer is lower than that of common monosilicon, the temperature of the silicide can maintain its original temperature as the heater circuit is heated. This enhances reliability of the heater circuit when the heater circuit operates for long periods.

The disclosure provides a gas sensor, comprised of a silicon on insulator (SOI) substrate and a sensing material. The SOI substrate includes an oxide layer, a device layer and a carrier. Wherein the oxide layer is disposed between the device layer and the carrier. The device layer includes an integrated circuit region, an outer region, at least one conducting line, and a trench. Since a gap exists between the integrated circuit region and the outer region, the outer region does not directly connect with the integrated circuit region. The conducting line includes a connecting arm connecting to the integrated circuit region. The trench is formed around the conducting line and excavated to the oxide layer for reducing power consumption due to heating from the heater circuit. The carrier further includes a cavity passing through the oxide layer and up to the gap so as to form a device layer film suspended in the cavity, wherein the device layer film connects with the SOI substrate by cantilever arms such as the above-mentioned connecting arms. The sensing material is coated on the integrated circuit region, wherein the integrated circuit region is suspended on the cavity and cantilevered by the connecting arm.

The disclosure provides a manufacturing method of a gas sensor. The manufacturing method comprises the following steps: providing a SOI substrate, including an oxide layer, a device layer, and a carrier, wherein the oxide layer is disposed between the device layer and the carrier; etching the device layer to form an integrated circuit region, an outer region, a trench and at least one conducting line, wherein the conducting line includes a connecting arm connecting to the integrated circuit region, the trench is formed around the conducting line and excavated to the oxide layer for reducing the power consumption of the heater circuit, the connecting arm reaches over a gap formed between the integrated circuit region and the outer region and electrically connects to the integrated circuit region; coating or imprinting a sensing material on the integrated circuit region; and etching the carrier and the oxide layer to form a cavity up to the gap so as to form a film structure, wherein the integrated circuit region is suspended on the cavity and cantilevered by the connecting arm The foregoing has outlined rather broadly the features and technical benefits of the disclosure in order that the detailed description of the disclosure that follows may be better understood. Additional features and benefits of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the invention as set forth in the appended claims.

BRIEF DESCRIPTION OF THE SEVERAL VIEWS OF THE DRAWINGS

The accompanying drawings, which are incorporated in and constitute a part of this specification, illustrate embodiments of the disclosure and, together with the description, serve to explain the principles of the disclosure.

DETAILED DESCRIPTION OF THE INVENTION

Figure 1A:
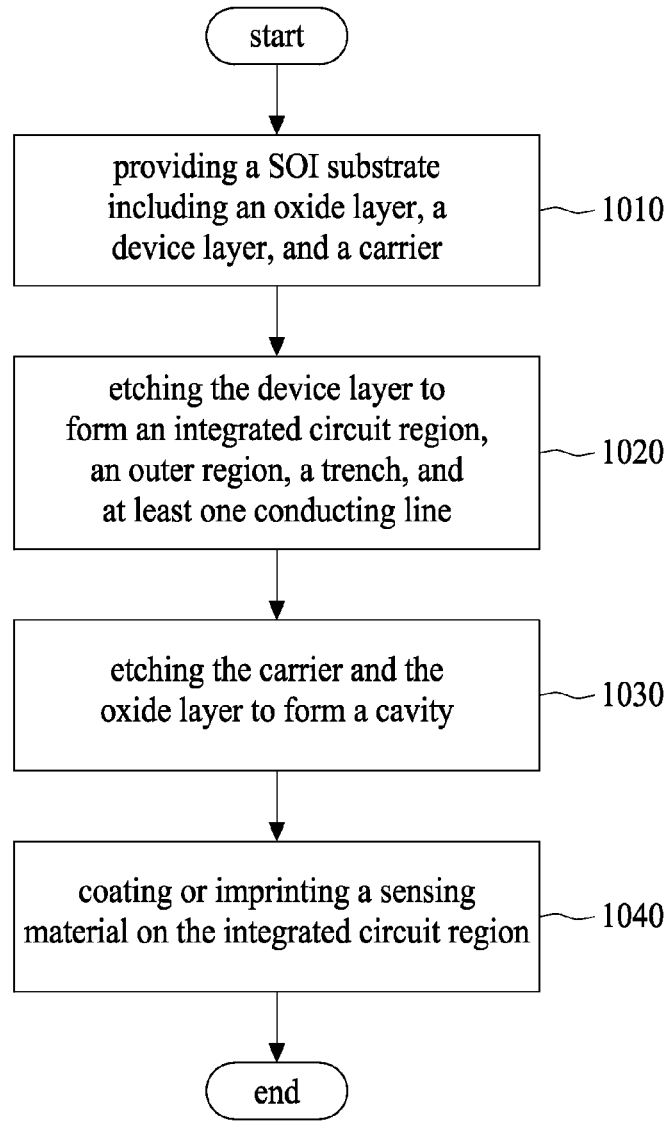
FIG. 1A is the process flow diagram of one exemplary embodiment of the manufacturing method of the gas sensor.

One exemplary embodiment of the disclosure is shown in the process flow diagram of FIG. 1A, the manufacturing method comprises the following steps: Step 1010 provides a SOI substrate, which includes an oxide layer, a device layer and a carrier, wherein the oxide layer is disposed between the device layer and the carrier; Step 1020 etches the device layer to form an integrated circuit region, an outer region, a trench, and at least one conducting line, wherein the conducting line includes a connecting arm connecting to the integrated circuit, the trench is formed around the conducting line and excavated to the oxide layer, a gap exists between the integrated circuit region and the outer region, and the connecting arm reaches over the gap and connects to the integrated circuit region. Step 1030 etches the carrier and the oxide layer to form a cavity, which opens up to the gap and Step 1040 coats or imprints a sensing material on the integrated circuit region, wherein the integrated circuit region is suspended on the cavity and cantilevered by the connecting arm. Besides, in another exemplary embodiment, the manufacturing method can perform Step 1040 before Step 1030, which means coating or imprinting a sensing material on the integrated circuit region and then etching the carrier and the oxide layer to form a cavity.

Figure 1B:
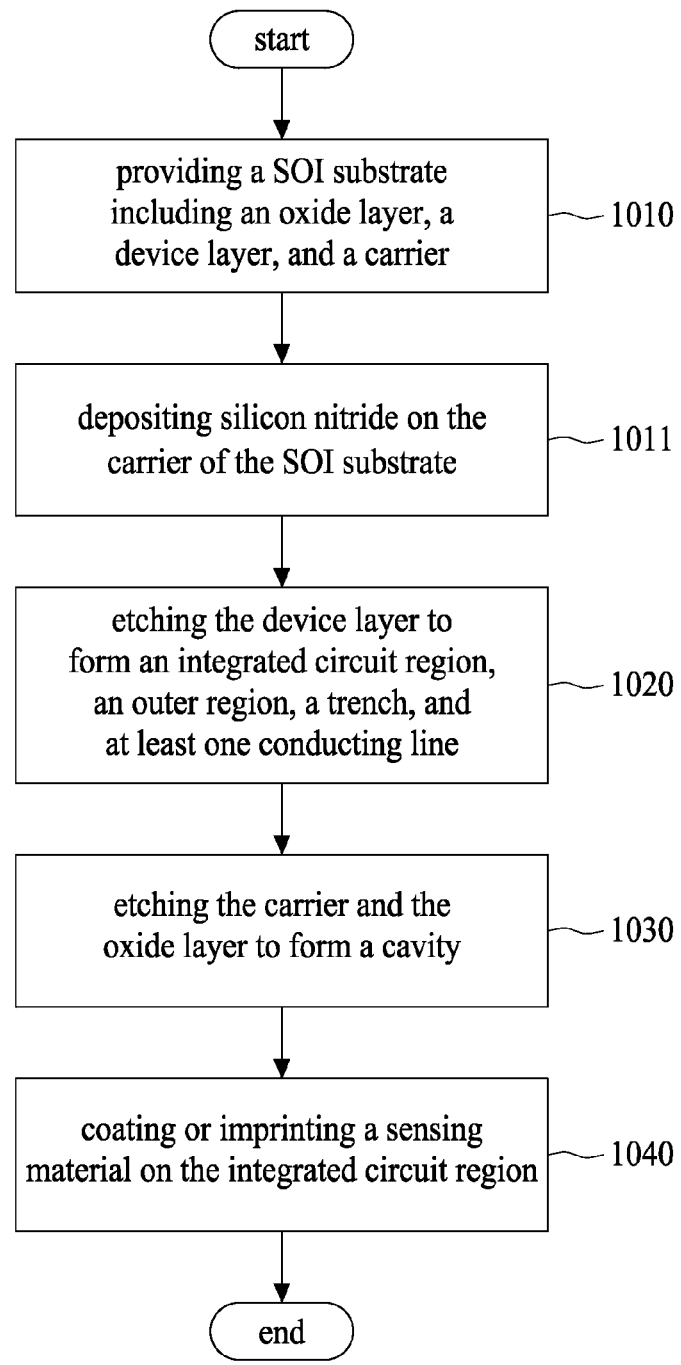
FIG. 1B is the process flow diagram of another exemplary embodiment of the manufacturing method of the gas sensor.

Another exemplary embodiment of the disclosure is shown in the process flow diagram of FIG. 1B, the manufacturing method further comprises steps 1011. Step 1011 deposits silicon nitride on the carrier of the SOI substrate.

Figure 1C:
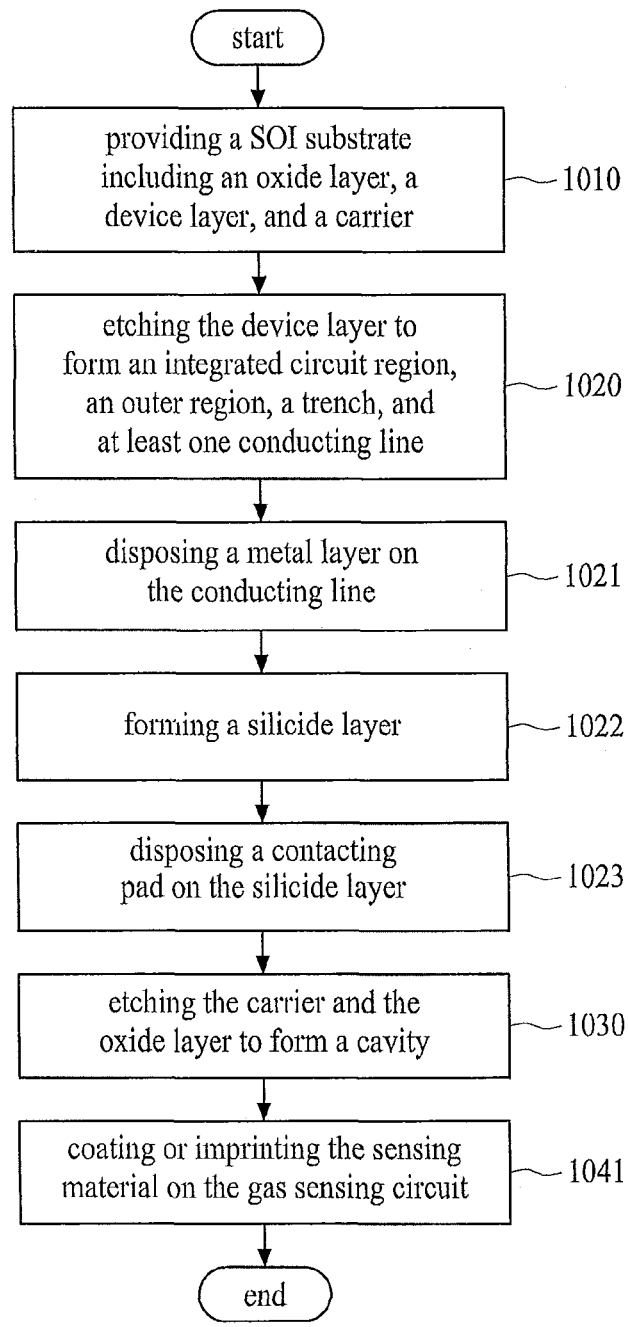
FIG. 1C is the process flow diagram of another exemplary embodiment of the manufacturing method of the gas sensor.

Another exemplary embodiment of the disclosure is shown in the process flow diagram of FIG. 1C, the manufacturing method further comprises steps 1021, 1022, 1023, and 1041. Step 1021, through a metal lift-off process, disposes a metal layer on the conducting line, wherein the integrated circuit region further includes a gas sensing circuit and a heater circuit. Step 1022 forms a silicide layer on the conducting line connected to the heater circuit. Step 1023 disposes a contacting pad on the silicide layer. The integrated circuit region is formed in Step 1020. The sensing material coating or imprinting step further includes Step 1041 coats or imprints the sensing material on the gas sensing circuit and sinters the sensing material.

Figure 1D:
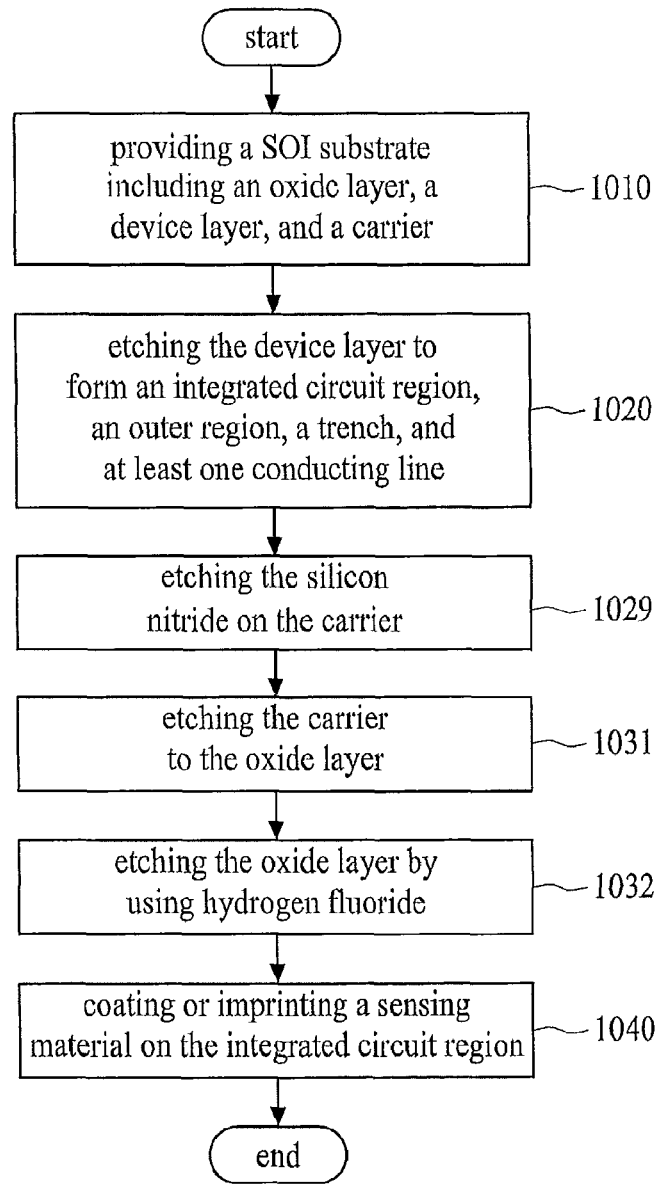
FIG. 1D is the process flow diagram of another exemplary embodiment of the manufacturing method of the gas sensor.

Another exemplary embodiment of the disclosure is shown in the process flow diagram of FIG. 1D, the manufacturing method further comprises steps 1029, 1031, and 1032. Step 1029 etches the silicon nitride on the carrier for defining the cavity area. The carrier and oxide layer etching step further includes step 1031 and step 1032. Step 1031 etches the carrier to the oxide layer so as to expose the oxide layer. Step 1032 etches the oxide layer using hydrogen fluoride to form a cavity passing through the oxide layer and opening up to the gap.

Figure 1E:
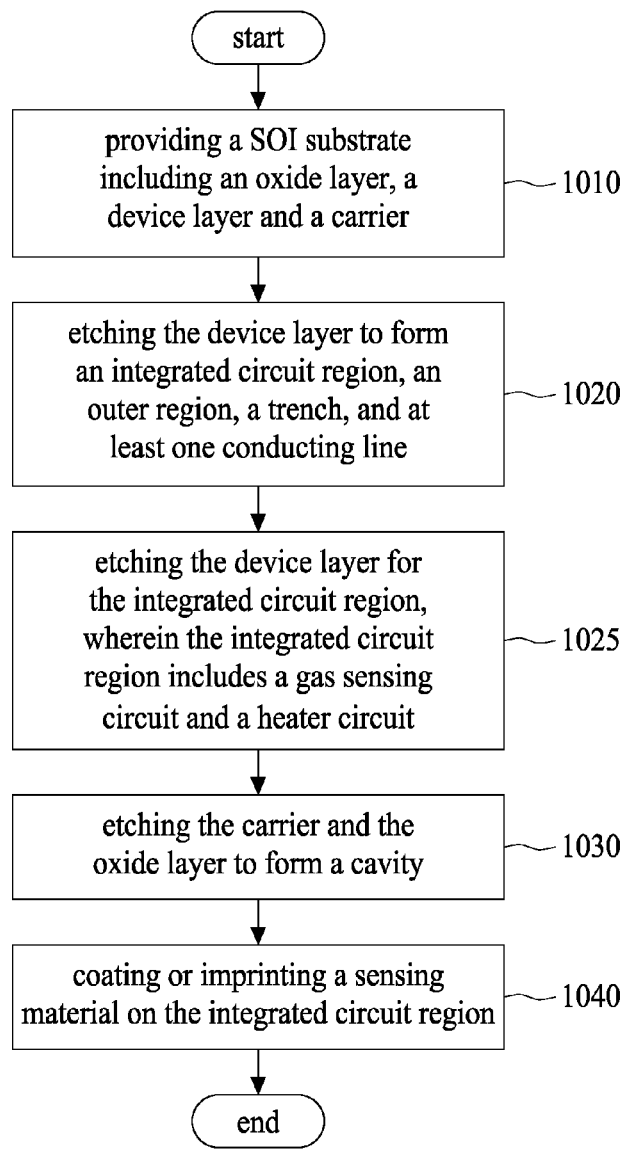
FIG. 1E is the process flow diagram of another exemplary embodiment of the manufacturing method of the gas sensor.

Another exemplary embodiment of the disclosure is shown in the process flow diagram of FIG. 1E, the device layer etching step 1020 further includes step 1025. Step 1025 etches the device layer for the integrated circuit region, wherein the integrated circuit region includes a gas sensing circuit and a heater circuit. It is noticeable that the above-mentioned steps can be combined to form certain practicable processes.

Figure 2A:
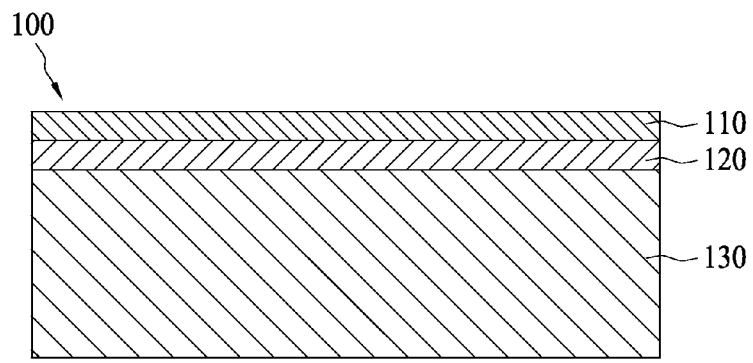
FIGS. 2A through 2K illustrate a method for fabricating a gas sensor in accordance with one exemplary embodiment.
Figure 2B:
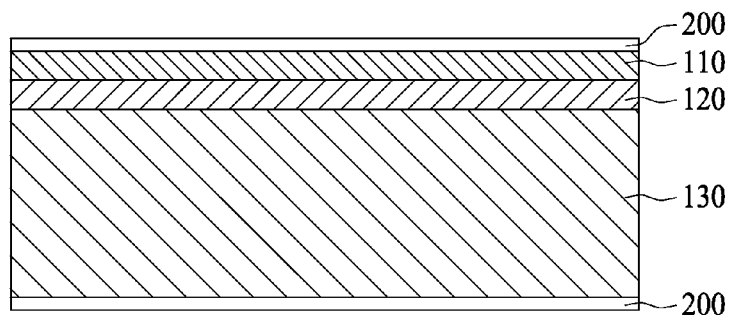
Figure 2C:
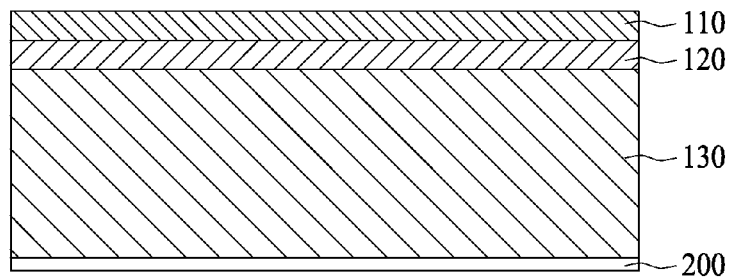
Figure 2D:
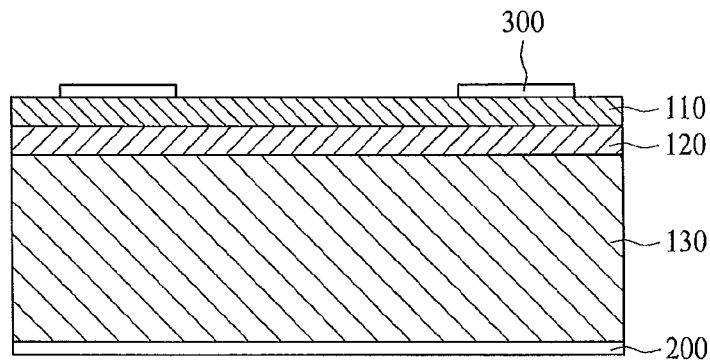
Figure 2E:
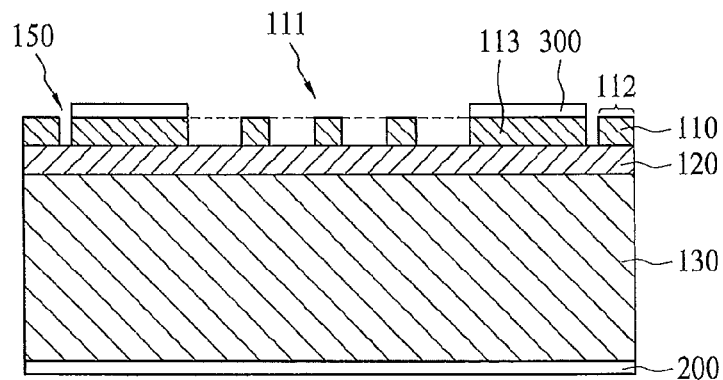
Figure 2F:
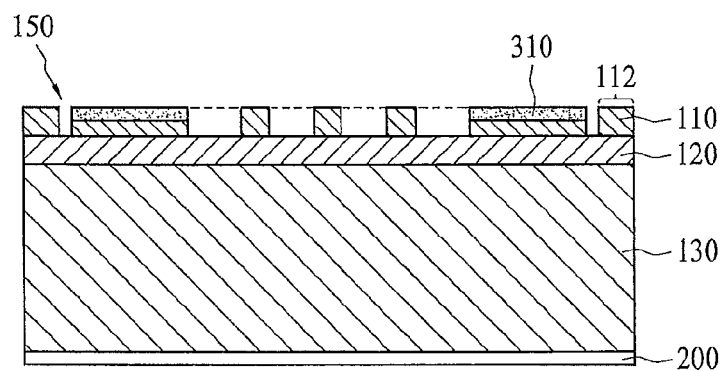
Figure 2G:
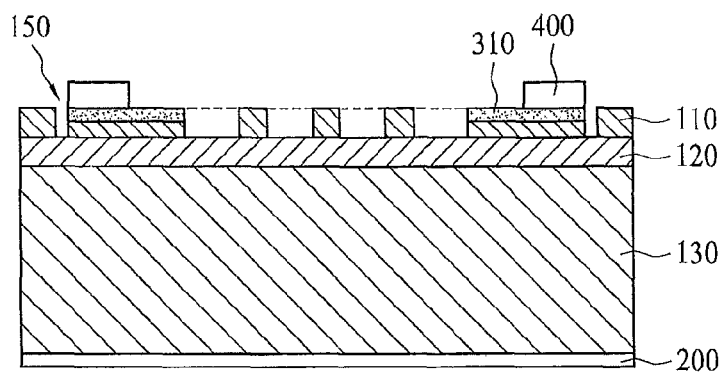
Figure 2H:
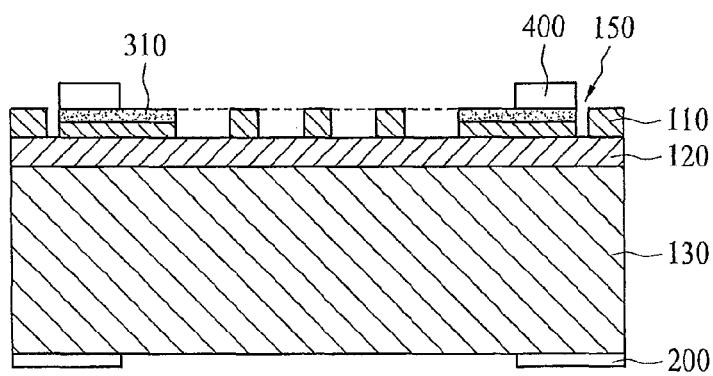
Figure 2I:
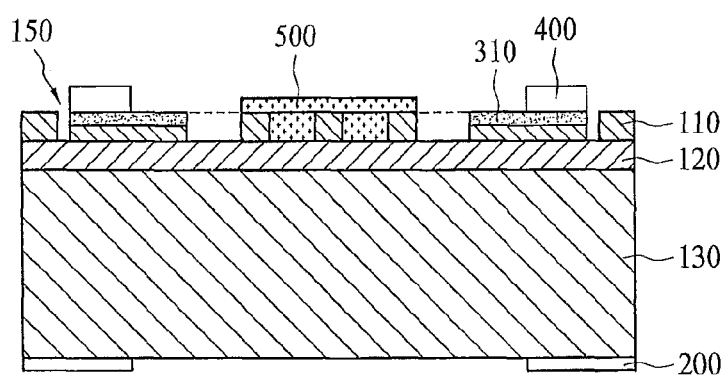
Figure 2J:
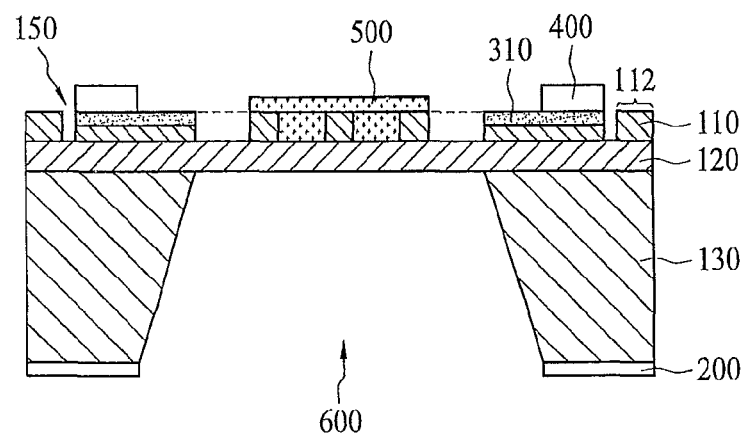
Figure 2K:
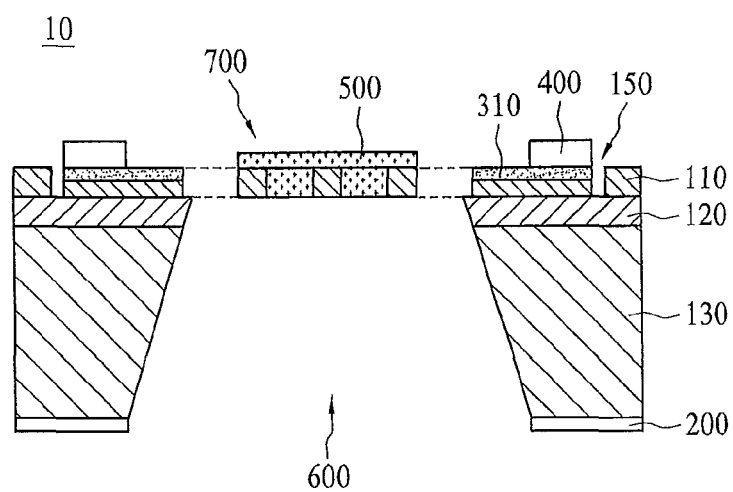

FIGS. 2A through 2K are cross-sectional views illustrating a method for forming a gas sensor in accordance with one exemplary embodiment. The cross-sectional view is shown in accordance with the cross-sectional line B-B of FIG. 3A. Referring to FIG. 2A, in one exemplary embodiment, manufacturing processes are performed to provide a low electrical resistance silicon on insulator (SOI) substrate 100, including a device layer 110, an oxide layer 120, and a carrier 130. The oxide layer 120 is disposed between the device layer 110 and the carrier 130. In this exemplary embodiment, the thickness of the carrier 130 is greater than that of the device layer 110. However, in other exemplary embodiments (not shown), the thickness of the carrier 130 can be less than or equal to that of the device layer 110. As shown in FIG. 2B, the SOI substrate 100 has been deposited by the silicon nitride 200 as a mask for a wafer back side etching process. As shown in FIG. 2C, in order to perform further processes on the device layer 110, the silicon nitride 200 on the device layer 110 has been removed. In addition, the silicon nitride 200 may be deposited at one side of the carrier 130 and thus the location of the silicon nitride is not limited in the embodiment of FIG. 28. If the silicon nitride is deposited at one side of carrier 130, the step illustrated in FIG. 2C can be abridged. Consequently, the first photolithographic process has been performed as shown in FIG. 2D, so that the metal layer 300 can be disposed on the predetermined region of device layer 110 by metal lift-off process. As shown in FIG. 2E, the second photolithographic process has been performed to etch the trench 150; meanwhile, the shape of the integrated circuit region 111 has been defined. The integrated circuit region 111 includes a heater circuit, a gas sensing circuit, and a temperature sensing circuit. As shown in FIG. 2F, through an annealing process, the metal layer 300 has diffused into the monosilicon of the device layer 110 to form a silicide layer 310. By such design, the electrical resistance of the silicide layer 310 can be reduced. When the heater circuit conducts electricity, since the electrical resistance of the silicide layer 310 is less than that of the heater circuit, most of the heat is generated by the heater circuit instead of by the silicide layer 310. Thus, the silicide layer 310 with low electrical resistance can reduce total power consumption from the heater circuit. As shown in FIG. 2G, the third photolithographic process is performed to dispose the contacting pad 400 on the silicide layer 310. FIG. 2H shows that the wafer back side photolithographic process is performed to etch the silicon nitride 200 on the carrier 130 so as to define the back side opening of the cavity. As shown in FIG. 2I, the sensing material 500 is coated or imprinted on the integrated circuit region 111 and sintered. Therefore, the monosilicon layer of the integrated circuit region including heater circuit, gas sensing circuit, and temperature sensing circuit is coated or imprinted by the sensing material to form a sensing film or device layer film. As shown in FIG. 2J, the wafer back side etching process is performed to etch the carrier 130 to the oxide layer 120 so as to form a cavity 600. Finally, as shown in FIG. 2K, the embedded oxide layer 120 is etched by hydrogen fluoride in gas phase to form a cantilevered sensing film 700 or device film. After wire bonding and packaging processes, the gas sensor 10 is completed.

Figure 3A:
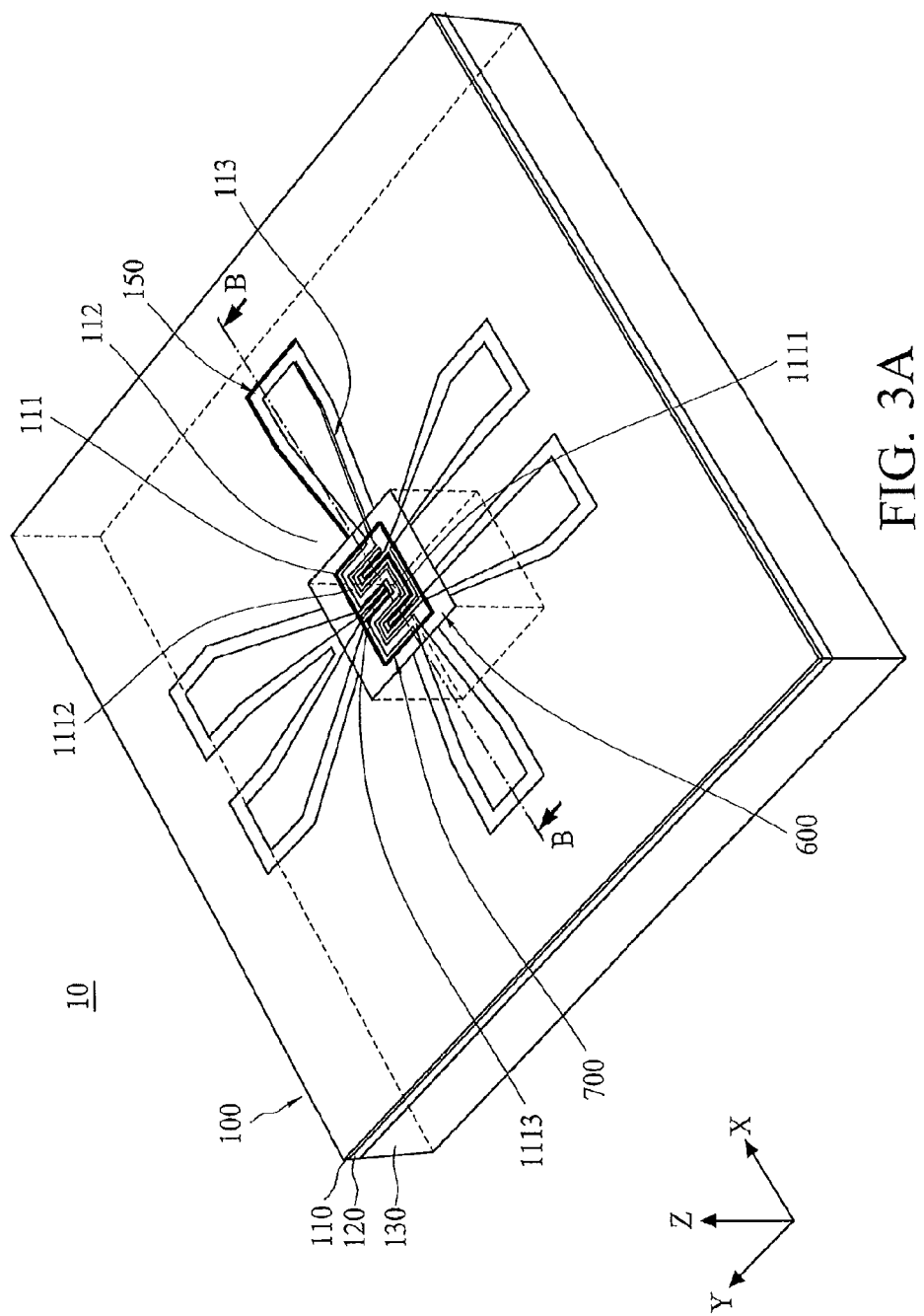
FIG. 3A illustrates a gas sensor in accordance with one exemplary embodiment of the disclosure.

FIG. 3A illustrates a gas sensor in accordance with one exemplary embodiment of the disclosure. As shown in FIG. 3A, a gas sensor 10 comprises a SOI substrate 100. The SOI substrate 100 includes a device layer 110, an oxide layer 120, and a carrier 130. The oxide layer 120 is disposed between the device layer 110 and the carrier 130. The carrier 130 of the gas sensor 10 includes a cavity 600, which passes through the oxide layer 120 and a gap existing between an integrated circuit region 111 and an outer region 112 to form the integrated circuit region 111 as a sensing film 700 structure. In the exemplary embodiment shown in FIG. 3A, the device layer 110 is made of monosilicon, which has low electrical resistance and is of a predetermined thickness so that the integrated circuit region of the device layer 110 can be easily integrated with sensing material 500 (shown in FIG. 2K) to form a sensing film 700 which is less vulnerable than the sensing film of the prior art. The device layer 110 includes the integrated circuit region 111, the outer region 112, at least one conducting line 113, and a trench 150. In the exemplary embodiment, the integrated circuit region 111 includes a gas sensing circuit 1111, a heater circuit 1112, and a temperature sensing circuit 1113. However, in other exemplary embodiments (not shown), the integrated circuit region 111 can include only the gas sensing circuit 1111 and the heater circuit 1112. This is possible because the heater circuit 1112 can heat the air in the cavity 600 so as to allow molecules in the air to attach to the sensing circuit 1111. Thus, in this exemplary embodiment, the temperature sensing circuit 1113 is unnecessary. The function of the temperature sensing circuit 1113 is to sense the temperature around the integrated circuit region 111 and to check whether the correct working temperature is reached. In the exemplary embodiment shown in FIG. 3A, the gas sensing circuit 1111, the heater circuit 1112, and the temperature sensing circuit 1113 are electrically insulated from each other. In other words, the gas sensing circuit 1111, the heater circuit 1112, and the temperature sensing circuit 1113 are electrically independent from each other.

Figure 3B:
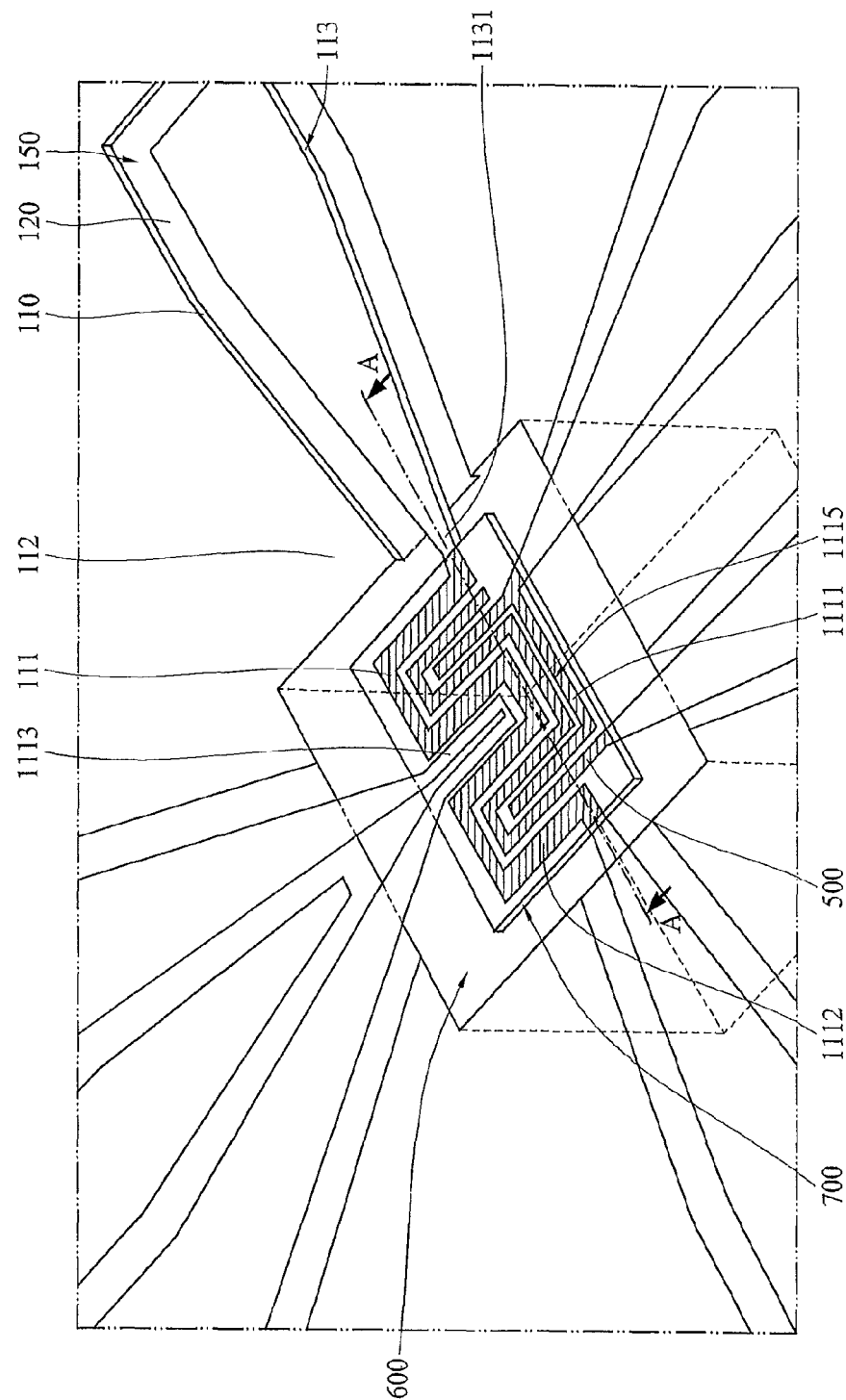
FIG. 3B is a zoom-in figure of FIG. 3A.

The details of the device layer 110 are shown in FIGS. 3A and 3B. The integrated circuit region 111 includes the heater circuit 1112, the temperature sensing circuit 1113, and the gas sensing circuit 1111, which includes at least one bending structure 1115. The gas sensor 10 further includes a sensing material 500, which is coated or imprinted on the gas sensing circuit 1111.

Figure 3C:
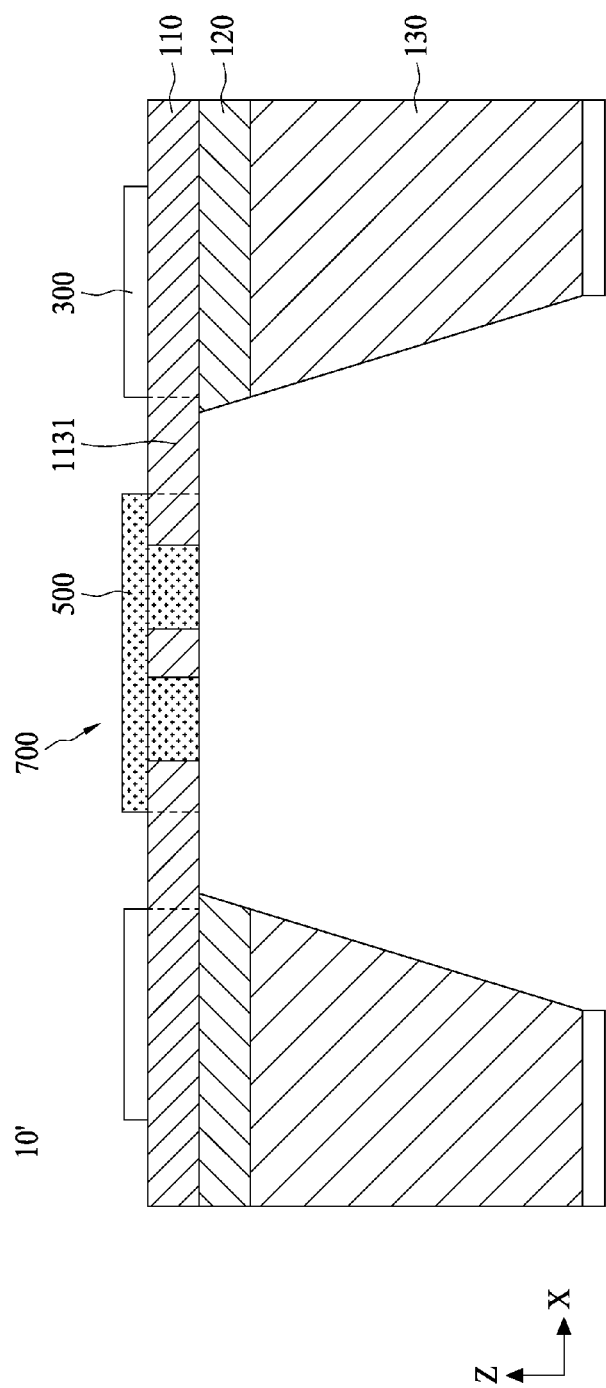
FIG. 3C is a cross-sectional view of line A-A in FIG. 3B.

In the exemplary embodiment shown in FIG. 3B, a gap exists between the outer region 112 and the integrated circuit region 111. The gap is connected to the cavity 600 to form the integrated circuit region 111 as a film 700 structure cantilevered by at least one of the conducting lines 113. The outer region 112 is located in relation to the integrated circuit region 111 but the outer region 112 doesn't include the conducting line 113 or the trench 150. The conducting line 113 has a connecting arm 1131, which connects to the integrated circuit region 111, wherein the conducting line 113 electrically connects to one of the circuits in the integrated circuit region 111. Thus, the connecting arm 1131 reaches over the gap between the integrated circuit region 111 and the outer region 112. Furthermore, because the trench 150 is formed around the conducting line 113 and excavated to the oxide layer 120, the trench 150 can expose the oxide layer 120. The trench 150 of the disclosure is excavated around the edge of the conducting line 113. In addition, the trench 150 is not filled with any material. Since air conducts little heat, the vacant trench 150 has a better thermal insulating effect. By such design, although heat generated from the heater circuit 1112 in the integrated circuit region 111 can be conducted to the conducting line 113, heat is not conducted to the outer region 112 due to the poor thermal conductivity of the oxide layer 120 and the air of the trench 150. Moreover, for reducing power consumption, the electrical resistance of the conducting line 113 connected to the heater circuit 1112 is less than the electrical resistance of the heater circuit 1112. Higher electrical resistance in components translates to greater heat generation. Since the electrical resistance of the heater circuit 1112 is greater than that of the conducting line 113, as the electrical current is conducted through the conducting line 113, most of the heat generates from the heater circuit 1112, instead of the conducting line 113 connected to the heater circuit 1112. In another exemplary embodiment, shown in FIG. 2F, the conducting line 113 connected to the heater circuit 1112 connects to a silicide layer 310. In another exemplary embodiment, shown in FIGS. 3C and 3B, a metal layer 300 is disposed on the conducting line 113 connected to the heater circuit 1112. FIG. 3C is a cross-sectional view of line A-A in FIG. 3B. As shown in FIG. 3C, the gas sensor 10' includes the device layer 110, the oxide layer 120, and the carrier 130. The sensing material 500 is coated or imprinted and sintered in the integrated circuit region 111 (shown in FIG. 3B). By such design, the sensing material 500, the heater circuit, the gas sensing circuit, and the temperature sensing circuit form a sensing film 700 structure, which has a low electrical resistance in the conducting line 113 (shown in FIG. 3B) connected to the heater circuit to reduce the power consumption of the conducting line.

Although the disclosure have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the disclosure is not intended to be limited to the particular embodiments of the process, machine, manufacturing, composition of matter, means, methods and steps described in the specification. As one of ordinary skill in the art will readily appreciate from the disclosure, processes, machines, manufacturing, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacturing, compositions of matter, means, methods, or steps.

We claim:

1. A gas sensor comprising:
an oxide layer;
a device layer including:
an integrated circuit region;
an outer region, wherein a gap exists between the integrated circuit region and the outer region;
at least one conducting line having a connecting arm connecting to the integrated circuit region; and
a trench formed around the conducting line and excavated to the oxide layer;
a carrier including a cavity passing through the oxide layer and up to the gap; and
a sensing material coated or imprinted on the integrated circuit region, wherein the integrated circuit region is suspended on the cavity and cantilevered by the connecting arm;
wherein the oxide layer is disposed between the device layer and the carrier.

2. The gas sensor of claim 1, wherein the device layer is made of monosilicon having low electric resistance.

3. The gas sensor of claim 1, wherein the integrated circuit region includes a gas sensing circuit and a heater circuit.

4. The gas sensor of claim 3, wherein the electric resistance of the conducting line connected to the heater circuit is less than the electrical resistance of the heater circuit.

5. The gas sensor of claim 4, wherein the conducting line connected to the heater circuit further comprises a silicide layer.

6. The gas sensor of claim 4, wherein the conducting line connected to the heater circuit has a metal layer atop the conducting line.

7. The gas sensor of claim 3, wherein the gas sensing circuit includes at least one groove.

8. The gas sensor of claim 7, wherein the sensing material is coated or imprinted atop the gas sensing circuit.

9. The gas sensor of claim 3, wherein the integrated circuit region further includes a temperature sensing circuit, wherein the gas sensing circuit, the heater circuit and the temperature sensing circuit are electrically insulated from each other.

* * * * *